US007309608B2

(12) United States Patent
Nguyen et al.

(10) Patent No.: US 7,309,608 B2
(45) Date of Patent: Dec. 18, 2007

(54) METHOD OF ANALYSIS OF ALDEHYDE AND KETONE BY MASS SPECTROMETRY

(76) Inventors: Hoa Duc Nguyen, 7735 E. Fieldcrest La., Orange, CA (US) 92869; Trinh Duc Nguyen, 2077 S. Sprague La. #1, Anaheim, CA (US) 92802; Duc Tien Nguyen, 14701 Bowling Green, Westminster, CA (US) 92683

( * ) Notice: Subject to any disclaimer, the term of this patent is extended or adjusted under 35 U.S.C. 154(b) by 781 days.

(21) Appl. No.: 10/675,763

(22) Filed: Sep. 30, 2003

(65) Prior Publication Data

US 2005/0070022 A1 Mar. 31, 2005

(51) Int. Cl.
*G01N 33/00* (2006.01)

(52) U.S. Cl. ........................ 436/128; 436/56; 436/111; 436/173; 436/175

(58) Field of Classification Search .................. 436/56, 436/128, 111, 106, 173, 177, 178
See application file for complete search history.

(56) References Cited

U.S. PATENT DOCUMENTS

| | | |
|---|---|---|
| 5,559,038 A | 9/1996 | Kolhouse |
| 6,358,996 B1 | 3/2002 | Alexander |

FOREIGN PATENT DOCUMENTS

| | | | |
|---|---|---|---|
| WO | 02/060565 | * | 8/2002 |

OTHER PUBLICATIONS

Ludeman, S. M. et al. (abstract) Journal of Pharmaceutical Sciences, vol. 84, No. 4, Apr. 1995, pp. 393-398.*

Bruenner, B A et al. Analytical Biochemistry, vol. 241, 1996, pp. 212-219.*

Zurek et al. Fresenius Journal of Analytical Chemistry, vol. 366, 2000, pp. 396-399.*

Zurek et al. Analyst, vol. 124, 1999, pp. 1291-1295.*

Zurek et al. Journal of Chromatography A, vol. 869, 2000, pp. 251-259.* van Kuijk et al. Analytical Biochemistry, vol. 224, 1995, pp. 420-424.*

Dennis J. Dietzen et al. Facilitation of Thin-layer Chromatographic Identification of Opiates by Derivatization With Acetic Anhydride and Methoxyamine. Journal of Analytical Toxicology, Sep. 1995, pp. 299-303, vol. 19.

Kyle R. Gee et al. Arene Chromium and Manganese Tricarbonyl Analogs of the PCP Receptor Ligands 5-methyl-10,11-dihydro-5-H-dibenzo[a,d]cycloheptene-5,10-imine (MK-801) and 10,5-(iminomethano)10-11-dihydro-5H-dibenzo[a,d]cycloheptene. Journal of Organic Chemistry 1994, pp. 1492-1498, vol. 59.

Hiroshi Goda et al. Facile Synthesis of 5-substituted-2-acetylthiophenes. Synthesis 1992, p. 849-851.

Arun K. Ghosh et al. Stereoselective Reduction of α-Hydroxy-oxime Ethers: A Convenient Route to cis-1,2-amino alcohols. Tetrahedron Letters, 1991, pp. 711-714, vol. 32.

* cited by examiner

*Primary Examiner*—Maureen M. Wallenhorst

(57) ABSTRACT

A method of identification and quantitative analysis of aldehydes and/or ketones in a sample by mass spectrometry using stable isotope labeled oxime internal standards or stable isotope labeled hydrazone internal standards is provided. Stable isotope labeled oxime internal standards are synthesized by reaction of an authentic sample of aldehydes and/or ketones with a stable isotope labeled alkoxylamine reagent while stable isotope labeled hydrazone internal standards are synthesized by reaction of an authentic sample of aldehydes and/or ketones with a stable isotope labeled alkylhydrazine reagent. A non labeled version of the stable isotope labeled reagent is used to convert aldehydes and/or ketones in the sample to the non labeled version of the stable isotope labeled oxime or hydrazone internal standards.

26 Claims, No Drawings

METHOD OF ANALYSIS OF ALDEHYDE AND KETONE BY MASS SPECTROMETRY

BACKGROUND OF THE INVENTION

This invention pertains to methods of quantitative analysis of aldehydes and ketones in a sample by isotope dilution mass spectrometry. The stable isotope labeled oximes and hydrazones are used as internal standards. The sample may be a biological fluid, such as serum, urine etc., or an aqueous sample such as an environmental or an agricultural sample.

While various methods of analysis such as immunoassays and chromatographic analysis—LC (liquid chromatography), GC (gas chromatography), and TLC (thin layer chromatography)—have been reported for identification and determination of levels of aldehydes and ketones in analytical samples, the absolute and unequivocal identification and quantitative analysis of those compounds are combinations of chromatographic analysis and MS (mass spectrometry) such as GC-MS and LC-MS. The accuracy and precision of these methods are usually the highest when stable isotope analogs of the analytes are used as internal standards. The mass spectrometry method of analysis using stable isotope internal standards is commonly called isotope dilution mass spectrometry. This method takes advantage of the similar chemical and physical behaviors of analytes and their respective isotope labeled internal standards towards all phases of sample preparation and also towards instrument responses. It uses the mass differentiation between analytes and their respective internal standard in mass spectrometry for quantification. The requirement for this method of analysis is the availability of stable isotope labeled internal standards.

The commonly used stable isotope labeled internal standard of an analyte is a chemical compound that has the same chemical structure as that of the analyte except that one or more substituent atoms are stable isotopes. Four commonly used stable isotopes are deuterium, carbon-13, nitrogen-15, and oxygen-18. For every hydrogen atom that is replaced by a deuterium atom, the molecular weight of resulting chemical compound is increased by one mass unit. This is also true for replacing a carbon atom with a carbon-13 atom, or by replacing a nitrogen atom with a nitrogen-15 atom. In the case of replacing an oxygen atom with an oxygen-18 atom, the molecular increase is two mass units. Although the acceptable stable isotope labeled internal standard for isotope dilution mass spectrometry method is the one that is not contaminated with any of the unlabeled material, the ideal one should be the one with the highest isotopic purity and contains as many stable isotope atoms as possible. The ideal one, however, must not contain any labeled isotope that can be exchanged for the unlabeled isotope under particular sample preparation conditions.

These criteria of an ideal stable isotope labeled internal standard present a challenge for organic synthesis chemists who help the analytical chemists in the analysis. Most often the synthesis of stable isotope internal standards is not simply an isotope exchange reaction. Easily exchangeable atoms are usually avoided due to possible re-exchange during sample preparation steps. Organic chemists often have to carry out multi-step synthesis to make stable isotope labeled internal standards. Even though many stable isotope labeled reagents are commercially available, the choice of appropriate labeled reagent for chemical synthesis of stable isotope labeled internal standards is still very limited. The limited isotope labeled reagents and the multi-step synthesis contribute to the high cost of synthesis of stable isotope internal standards. Even if the analytical chemist who carries out the analysis can afford the cost of the synthesis, there is also a time factor that he or she has to consider before ordering the synthesis. Situations where organic chemists spent weeks and months on a synthesis project and came up with nothing at the end were common. This invention offers a solution for this problem.

The objective is a short and reliable method of preparing a stable isotope labeled internal standard that is suitable for the analysis of an analyte in question, but not the synthesis of the stable isotope labeled analyte. Within the context of the isotope dilution mass spectrometry method, both analyte and its internal standard have to have identical chemical structures, with the exception of the isotope atoms which provide the mass differentiation upon mass spectrometric analysis. Analytical chemists who uses GC-MS for their analysis often "derivatize" the analyte and its stable isotope labeled analyte (used as internal standard) into chemical compounds that can easily pass through the GC column or else provide better instrumental responses. The analysis becomes the analysis of the "derivatized" analyte and the "derivatized" internal standard, but still provides comparably accurate results of concentrations of the analyte itself. Examples of these analyses are found in cited references. Using similar reasoning, one can synthesize a stable isotope derivative of the analyte by reacting it with a stable isotope labeled reagent. The resulting isotope labeled chemical compound can be used as internal standard in the analysis of the analyte, providing that the analyte in the analyzed sample will be converted to a chemical compound of identical structure as that of the internal standard using a non-labeled reagent. There are 3 requirements for the usefulness of this method:

1. The analyte in the sample must be quantitatively converted to the compound of identical structure (except the labeled atoms) as that of the added isotope labeled internal standard using a non-labeled reagent.
2. Absolutely no conversion of the isotope labeled internal standard to the non-labeled compound because the conversion of the analyte happens in the sample in the presence of the added isotope labeled internal standard.
3. The conversion of the analyte into the compound of identical structure as that of the added isotope labeled internal standard has to be accomplished before any isolation method i.e. extraction, is performed.

The first two requirements relate to the chemistry of the analyte in question. The efficiency of a chosen chemical reaction depends on the type of reaction which, in turn, depends on the type of functional groups of the analyte. This invented method relates to the analysis of aldehydes and ketones whose chemistry focus on the reactivity of the carbonyl functional groups of the analyte.

Quantitative reactions of aldehydes and ketones in aqueous samples are:

1. Conversion to an oxime using an alkoxyl amine.
2. Conversion to a hydrazone using an alkyl hydrazine.

There are other reactions of aldehydes and ketones that are very efficient, but the above conversion reactions are very efficient in aqueous environment and can be performed at room temperature and in a relatively short reaction time. These are necessary and practical features for routine analysis of aldehydes and ketones in aqueous samples.

BRIEF SUMMARY OF THE INVENTION

The current invention provides for a method of identification and quantification of aldehyde(s) and/or ketone(s) in a sample by isotope dilution mass spectrometry. The stable isotope labeled internal standard(s) of said aldehyde(s) and/or ketone(s) is synthesized beforehand by reacting a sample containing said analyzed aldehyde(s) and/or ketone(s) with a labeled reagent. Following this step, said stable isotope labeled internal standard(s) is then added to a sample containing said analyzed aldehyde(s) and/or ketone(s). Said analyzed aldehyde(s) and/or ketone(s) is then converted to a non labeled analog(s) of said labeled internal standard(s) with identical chemical structure as said labeled internal standard(s) except for the stable isotope atoms using a non-labeled reagent. Both said converted analyzed aldehyde(s) and/or ketone(s) and its corresponding said stable isotope labeled internal standard(s) are then extracted and analyzed by mass spectrometry. Said stable isotope labeled internal standard(s) provided in the current invention are labeled oxime(s) and hydrazone(s) analogs of said analyzed aldehyde(s) and/or ketone(s). The type of labeled internal standard(s) used will dictate the labeled reagents used for its synthesis as well as the non-labeled reagent used to convert the analyzed aldehyde(s) and/or ketone(s) to the corresponding analog(s).

In comparison with the traditional method of isotope dilution mass spectrometric analysis of more than one aldehydes and/or ketones, the invented method offers the following advantages:

1. The efficiency and simplicity of the above reactions makes possible the short, reliable, and quick synthesis of individual stable isotope labeled internal standards, whereas in the traditional method of analysis, stable isotope labeled internal standard of each aldehyde and/or ketone has to be independently synthesized.
2. It is possible to quickly and efficiently synthesize a library of stable isotope internal standards for the analysis of an entire library of aldehydes and/or ketones using these reactions and only one commercially available stable isotope labeled reagent.
3. Because the synthesis of stable isotope labeled internal standard in this invented method is usually a one-step synthesis, the entire process of synthesis and sample preparation can be performed in an automated fashion. The internal standard is prepared in one step, excess isotope reagent is then removed or destroyed, and the prepared internal standard can be added directly to the samples without purification. The non-labeled reagent is added and the sample is ready for extraction shortly thereafter.

These attractive features make the method suitable for high throughput analysis of aldehydes and/or ketones by isotope dilution mass spectrometry.

DETAILED DESCRIPTION OF THE INVENTION

The current invention provides for a method of identification and quantification of aldehyde(s) and/or ketone(s) in a sample by mass spectrometry. Said aldehyde(s) and/or ketone(s) has the following formulas $R_1CHO$, and $R_1R_2CO$, wherein $R_1$ and $R_2$ are alkyl, aryl, and heteroatom containing cyclic or non-cyclic groups. The current method comprises, as an intergral part of the analysis of said aldehyde(s) and/or ketone(s), the following steps:

1. Synthesizing labeled oxime internal standard(s) by reacting an authentic sample of said aldehyde(s) and/or ketone(s) with a stable isotope labeled reagent to form said oxime internal standard(s) of the general formulas $R_1CH{=}NOR_3$ or $R_1R_2C{=}NOR_3$, wherein $R_3$ is a stable isotope labeled alkyl group. Said $R_3$ stable isotope labeled alkyl group is selected from the group consisting of $CD_3$, and $CD_2C_6D_5$. Said stable isotope labeled reagent is a labeled alkoxyl amine selected from the group consisting of labeled methoxylamine and benzyloxyamine.
2. A known amount of said stable isotope labeled oxime internal standard(s) was then added to said sample containing said aldehyde(s) and/or ketone(s) to be analyzed.
3. Said sample was then contacted with a non-labeled alkoxylamine selected from said group consisting of methoxylamine and benzyloxyamine to quantitatively convert said aldehyde(s) and/or ketone(s) in the sample into said oxime(s) of identical structure as that of said oxime internal standard(s) mentioned above except for the stable isotope atoms.
4. Appropriate extraction methods were then used to isolate said oxime(s) and their corresponding oxime internal standard from said sample. Concentration of said oxime(s) were determined and quantified by mass spectrometry and based on the ratio of said converted oxime(s) and their corresponding oxime internal standard.

In another aspect of the present invention, said labeled internal standard is a stable isotope labeled hydrazone. In this embodiment, said stable isotope labeled hydrazone(s) is synthesized by reacting an authentic sample of said aldehyde(s) and/or ketone(s) with a stable isotope labeled reagent to form said hydrazone internal standard having the following formula $R_1CH{=}NNHR_3$ or $R_1R_2C{=}NNHR_3$ wherein $R_3$ is a stable isotope labeled alkyl group selected from the group consisting of $CD_3$, and $CD_2C_6D_5$. Said stable isotope labeled reagent is a labeled hydrazine selected from a group consisting of labeled methyl hydrazine and labeled benzyl hydrazine. Also, in this embodiment, said analyzed aldehyde(s) and/or ketone(s) is converted to a hydrazone of identical structure as that of said hydrazone internal standard except for the stable isotope atoms by contacting said sample with a non-labeled alkylhydrazine selected from a group consisting of methylhydrazine and benzylhydrazine.

EXAMPLE

Analysis of Donepezil in Human Plasma

Step 1: Preparation of Donepezil methoxyloxime-d3.

A solution of 5 mg of Donepezil in 0.5 ml tetrahydrofuran was treated with 10 equivalents of hydroxylamine hydrochloride and 0.5 ml 5N sodium hydroxide. The resulting solution was stirred for 20 hours then the reaction solution was extracted with ethyl acetate-hexane mixture. The combined organic extracts were dried with magnesium sulfate and filtered. The filtered solution was concentrated to give 2 mg crude donepezil oxime. This crude donepezil oxime was dissolved in 0.5 ml tetrahydrofuran and was treated with 1 mg 60% sodium hydride in mineral oil. After 15 minutes of stirring, 3 equivalents of iodomethane-d3 was added and the reaction continued to stir for 2 hr. the reaction was concentrated and was quenched with 1 ml of water. The quenched reaction was extracted with ethyl acetate-hexane mixture and the combined extracts were dried and concentrated. The residue was purified by column chromatography using silica gel as absorbant and hexane ethyl acetate mixture as eluant. The fractions containing clean Donepezil methoxyl oxime-d3 were combined and concentrated to give 0.5 mg product as an oil. MS analysis gave MH+412.

Step 2: Preparation of Working Standard Solutions and Internal Standard Solution.

Working standard solutions of donepezil were prepared by weighing donepezil and diluting the stock solution to appropriate concentration as follows:

| | | |
|---|---|---|
| Solution A | 2 ng/ml | in ethyl acetate |
| B | 5 ng/ml | |
| C | 10 ng/ml | |
| D | 20 ng/ml | |
| E | 100 ng/ml | |

Working quality control standard solutions of donepezil were prepared by independently weighing donepezil and diluting the stock solution to appropriate concentration as follows

| | | |
|---|---|---|
| QC Solution J | 3 ng/ml | in ethyl acetate |
| K | 70 ng/ml | |

Working internal standard solution of donepezil were prepared by preparing a stock solution of donepezil methoxyloxime-d3 and diluting the stock solution to a working concentration of 10 ng/ml in ethyl acetate.

Step 3: Preparation of Calibration Samples and Quality Control Samples in Human Plasma.

Donepezil-free human plasma aliquots of 0.1 ml were treated with 1000 ul of solution A to G to make calibration samples A to G.

Donepezil-free human plasma aliquots of 0.1 ml were treated with 1000 ul of solution J and K to make quality control samples J and K.

Both calibration samples and quality control samples were then treated with 400 ul of the internal standard working solution.

Step 4: Conversion to Oximes and Extraction.

To all prepared samples were added 10 ul of 5N aqueous sodium hydroxide followed by 100 ul of a 100 mg/ml solution of methoxylamine hydrochloride in water. The samples were mixed and shaked at room temperature for 30 minutes. The samples were extracted with 0.5 ml ethyl acetate. Each extract was separated and concentrated. The residue of each extract was reconstituted with 100 ul of acetonitrile.

Step 5: Analysis of Reconstituted Extracts by LC/MS/MS.

A total of 7 reconstituted extracts were loaded on a Perkin Elmer autosampler that was connected to a Perkin Elmer LC pump and a PE Sciex API 365 MS. Each extract was run through an Symmetry C-18 column of 5 um at a rate of 0.3 ml/min of acetonitrile/water 50/50 mixture. The eluate was directly fed to the MS ion source. MS data were collected for 1.5 min per injection.

MS analysis was performed in MRM mode. m/z 409.2>m/z 185.0 was monitored for donepezil methoxyloxime while m/z 412.2>m/z 185.0 was monitored for donepezil methoxyloxime-d3. Collected data were ploted against concentration using McQuan 1.5 sofware. Results are tabulated as follows:

Donepezil

Internal Standard: is

Weighted (1/x*x)

Intercept=3.073

Slope=0.101

Correlation Coeff.=0.999

Use Area

| Filename | Filetype | Accuracy | Conc. | Calc. Conc. | Int. Ratio |
|---|---|---|---|---|---|
| Keto A | Standard | 100.711 | 2.000 | 2.014 | 3.276 |
| Keto B | Standard | 98.088 | 5.000 | 4.904 | 3.567 |
| Keto C | Standard | 97.983 | 10.000 | 9.798 | 4.060 |
| Keto D | Standard | 104.914 | 20.000 | 20.983 | 5.186 |
| Keto E | Standard | 98.304 | 100.000 | 98.304 | 12.971 |
| Keto J | QC | 95.618 | 3.000 | 2.869 | 3.362 |
| Keto K | QC | 95.512 | 70.000 | 66.859 | 9.805 |

REFERENCES

| U.S. patent documents | | |
|---|---|---|
| 5,559,038 | Sep. 24, 1996 | J. Fred Kolhouse |
| 6,358,996 | Mar. 19, 2002 | Michael S. Alexander |

Other References

Dennis J. Dietzen et al, “Facilitation of thin-layer chromatographic identification of opiates by derivatization with acetic anhidride or methoxyamine”, *Journal of Analytical Toxicology*, Sep 1995, page 299-303, vol.

Kyle R. Gee et al, “Arene chromium and manganese tricarbonyl analogs of the PCP receptor ligands 5-methyl-10,11-dihydro-5-H-dibenzo[a,d]cyclohepten-5,10-imine (MK-801) and 10,5-(iminomethano)-10-11-dihydro-5H-dibenzo[a,d] cycloheptene” *Journal of Organic Chemistry*, 1994, p. 1492-1498, vol. 59.

Hiroshi Goda et al, “Facile synthesis of 5-substituted 2-acetylthiophenes”, Synthesis, 1992, p.849-851.

Arun K. Ghosh et al, “Steroselective reduction of alpha-hydroxy oxime ethers: a convenient route to cis-1,2amino alcohols”, Tetrahedron Letters, 1991,p.711-714, vol.32.

We claim:

1. A method of one-step chemical synthesis of stable isotope labeled internal standards and chemical reaction for the purpose of identification and quantification of aldehydes and/or ketones in an aqueous sample comprising the steps of synthesizing isotopically labeled oxime internal standards by reation of authentic samples of aldehydes and ketones with an isotopically labeled alkoxylamine reagent b) combining a known amount of said oxime internal standards with said sample comprising said aldehydes and/or ketones;

c) contacting said sample having the internal standards therein with an alkoxylamine to convert said aldehydes and/or ketones in said sample into oximes of identical structure as that of said oxime internal standards except for the stable isotope atoms wherein there is no conversion of said stable isotope labeled oxime internal standards to their corresponding non-labeled oxime compound during step c); and d) isolating said oximes and said oxime internal standards by aqueous extraction;

e) analyzing said oximes and said oxime internal standards by mass spectrometry.

2. The method of claim 1 wherein said aldehydes and/or ketones have the following formulas $R_1CHO$ and $R_1R_2CO$, respectively, wherein $R_1$ and $R_2$, are alkyl, aryl, and heteroatom containing cyclic or non-cyclic groups.

3. The method of claim 1 wherein said oxime internal standards are stable isotope labeled internal standards.

4. The method of claim 1 wherein said oxime internal standards are synthesized by reacting an authentic sample of aldehydes and/or ketones with a stable isotope labeled alkoxylamine reagent to form said oxime internal standards having the following formula $R_1CH{=}NOR_3$ or $R_1R_2C{=}NOR_3$, wherein $R_1$ and $R_2$ are alkyl, aryl, and heteroatom containing cyclic or non-cyclic groups and $R_3$ is a stable isotope labeled alkyl group.

5. The method of claim 4 wherein said labeled group $R_3$ is selected from a group consisting of $CD_3$ and $C_6D_5$, formed by reacting said aldehyde and/or ketone with labeled alkoxylamine selected from a group consisting of labeled methoxylamine and labeled benzyloxyamine.

6. The method of claim 1 wherein said aqueous extraction in step d) is any appropriate separating method such as solid phase extraction, liquid-liquid extraction or solid supported liquid-liquid extraction.

7. The method of claim 1 wherein said alkoxylamine is selected from a group consisting of methoxylamine and benzyloxyamine.

8. The method of claim 1 wherein said sample contains either a singularity or a plurality of aldehyde and/or ketone.

9. The method of claim 1 wherein said aldehydes and/or ketones are converted to said oximes using a single alkoxylamine.

10. The method of claim 1 wherein said labeled oxime internal standards are synthesized from said aldehydes and/or ketones using a single labeled alkoxylamine.

11. The method of claim 1 wherein said converting step c) is performed in an aqueous environment.

12. The method of claim 1 wherein said converting step c) is performed before said extraction step d).

13. The method of claim 1 wherein said converting step c) is quantitative.

14. A method of one-step chemical synthesis of stable isotope labeled internal standards and chemical reaction for the purpose of identification and quantification of aldehydes and/or ketones in an aqueous sample comprising the steps of:

synthesizing isotopically labeled hydrazone internal standards by reation of authentic samples of aldehydes and ketones with an isotopically labeled alkylhydrazine reagent b) combining a known amount of said hydrazone internal standards with said sample comprising said aldehydes and/or ketones;

c) contacting said sample having the internal standards therein with an alkylhydrazine to convert said aldehydes and/or ketones in said sample into hydrazones of identical structure as that of said hydrazone internal standards except for the stable isotope atoms; wherein there is no conversion of said stable isotope labeled hydrazone internal standards to their corresponding non-labeled hydrazone compound during step c)

d) isolating said hydrazones and said hydrazone internal standards by aqueous extraction; and e) analyzing said hydrazones and said hydrazone internal standards by mass spectrometry.

15. The method of claim 14 wherein said aldehydes and ketones have the following formulas $R_1CHO$ and $R_1R_2CO$, respectively, wherein $R_1$ and $R_2$ are alkyl, aryl, and heteroatom containing cyclic or non-cyclic groups.

16. The method of claim 14 wherein said hydrazone internal standards are stable isotope labeled internal standards.

17. The method of claim 14 wherein said hydrazone internal standards are synthesized by reacting an authentic sample of aldehydes and/or ketones with a stable isotope labeled alkylhydrazine reagent to form said hydrazone internal standards having the following formula $R_1CH{=}NNHR_3$ or $R_1R_2C{=}NNHR_3$, wherein $R_1$ and $R_2$ are alkyl, aryl, and heteroatom containing cyclic or non-cyclic groups and $R_3$ is a stable isotope labeled alkyl group.

18. The method of claim 17 wherein said labeled group $R_3$ is selected from a group consisting of $CD_3$ and $C_6D_5$, formed by reacting said aldehydes and/or ketones with labeled alkylhydrazine selected from a group [comprising] consisting of labeled methyxhydrazine and labeled benzylhydrazine.

19. The method of claim 14 wherein said aqueous extraction in step d) is any appropriate separating method such as solid phase extraction, liquid-liquid extraction or solid supported liquid-liquid extraction.

20. The method of claim 14 wherein said alkylhydrazine is selected from a group consisting of methylhydrazine and benzylhydrazine.

21. The method of claim 14 wherein said sample contains either a singularity or a plurality of aldehyde and/or ketone.

22. The method of claim 14 wherein said aldehydes and/or ketones are converted to said hydrazones using a single alkylhydrazine.

23. The method of claim 14 wherein said labeled hydrazone internal standards are synthesized from said aldehydes and/or ketones using a single labeled alkylhydrazine.

24. The method of claim 14 wherein said converting step c) is performed in an aqueous environment.

25. The method of claim 14 wherein said converting step c) is performed before said extraction step d).

26. The method of claim 14 wherein said converting step c) is quantitative.

* * * * *